Figure 1:
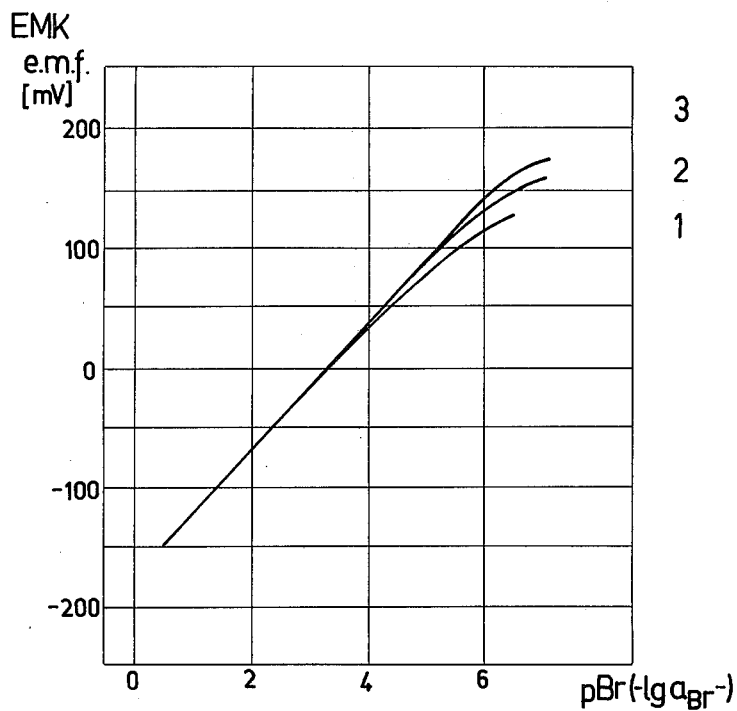

United States Patent [19]

Havas et al.

[11] 4,116,796
[45] Sep. 26, 1978

[54] SELECTIVE HALIDE AND SULFIDE SENSITIVE ELECTRODES

[75] Inventors: Jenö Havas; Elek Doktor; Marton Patko; Ernö Pungor, all of Budapest, Hungary

[73] Assignee: Radelkis Elektrokèmiai Müszergyarto Szövetkezet, Budapest, Hungary

[21] Appl. No.: 780,264

[22] Filed: Mar. 23, 1977

Related U.S. Application Data

[63] Continuation-in-part of Ser. No. 570,655, Apr. 23, 1975, abandoned.

[51] Int. Cl.² .................................... G01N 27/46
[52] U.S. Cl. ............................ 204/195 M; 204/1 T
[58] Field of Search ........... 204/1 F, 1 T, 1 B, 195 M

[56] References Cited

U.S. PATENT DOCUMENTS

| 3,607,710 | 9/1971 | Farren et al. | 204/195 M |
| 3,672,962 | 6/1972 | Frant et al. | 204/1 F |
| 3,822,198 | 7/1974 | Bauke | 204/195 M |
| 3,824,171 | 7/1974 | Van Houwelingen et al. | 204/195 M |
| 3,855,097 | 12/1974 | Sharpe et al. | 204/195 M |
| 3,879,279 | 4/1975 | Bauke | 204/195 M |
| 3,892,833 | 7/1975 | Hattori et al. | 204/195 M |

Primary Examiner—T. Tung

[57] ABSTRACT

Highly sensitive, selective halide and sulfide-sensitive electrodes featuring a sensing block of spherical surface and laminar design compensating for the effect of thermal dilatation and the absence of a liquid junction.

4 Claims, 2 Drawing Figures

SELECTIVE HALIDE AND SULFIDE SENSITIVE ELECTRODES

CROSS REFERENCE TO RELATED APPLICATION

This application is a continuation-in-part of U.S. Serial No. 570,655 filed April 23, 1975, now abandoned.

The invention relates to highly sensitive, selective halide- and sulfide-sensitive electrodes featuring a sensing block of spherical surface and laminar design compensating the effect of thermal dilatation, further the absence of a liquid junction; as well as to a process for the preparation thereof.

The development of measuring electrodes capable of rapid, highly sensitive and continuous determination of the rapid concentration of halide and sulfide ions is a requirement urgently needed in connection with the measurement of water and air pollution. Similar requirements are encountered by those working in the field of water analysis further in the analysis of foodstuffs, cosmetics, biological materials and fluids, etc.

From among the known methods, one of the fastest and most sensitive is the potentiometric measuring technique. The essence of this method is that a halide- or sulfide-sensitive electrode is placed into the solution to be tested and calculations of the halide or sulfide ion concentration of the solution can be made on the basis of the magnitude of the potential developed at the electrode.

Ion-sensitive electrodes have been described and have either heterogeneous or homogeneous membranes. For example, U.S. Pat. No. 3,446,726 deals with such ion-sensitive heterogeneous membrane, whereas British Pat. No. 1,150,698 described homogeneous membrane electrodes.

Heterogeneous membrane electrodes are prepared in such a manner that a salt sparingly soluble in a given solvent, e.g. water, a so-called precipitate — in the case of a halide-sensitive electrode, for example a precipitate of silver bromide — is homogenized in a silicone rubber monomer and the homogenizate is cured after having formed a membrane therefrom. A portion of the rubber membrane, containing the precipitate as a filter, is secured to the end of a tube; an electrolyte is placed into the tube and a potential outlet terminal is placed into the electrolyte.

Homogeneous membrane electrodes are prepared in such a manner that the precipitate — e.g. a precipitate of silver bromide — is compressed to form a membrane or else the precipitate is processed to a single crystal and the latter is formed into a wafer (membrane). A portion of the crystalline membrane thus prepared is cemented to the end of a tube and in the following procedure is similar to that described in connection with heterogeneous membrane electrodes.

Electrodes produced by the known procedures do not fulfill totally the requirements set in connection with them. Heterogeneous rubber membrane electrodes are vulnerable and are operative only for a period of a few months; the known homogeneous membrane electrodes tend to crack at the junction of the sensor crystal wafer, e.g. silver bromide crystal wafer, and the plastic electrode body, and, as a consequence of this, they show "memory effects". (Memory is the phenomenon which occurs when the electrode delivers ions from the previous sample, bound e.g. in the cracks, into the next sample solution, thereby altering composition of the latter.) This phenomenon falsifies the measured results, on the one hand, and, on the other, it considerably increases, to a three- to five-fold value, the time required to reach equilibrium potential, i.e. the response time of the electrode.

The sensitivity of the known homogeneous membrane electrodes is lower by at least one order of magnitude than that attainable as per our present knowledge. In addition, diffusion potentials, brought about as the consequence of ion transport across the membrane — as interfering signals — decrease the sensitivity of the electrode. Most of the reference electrodes placed into the internal electrolyte solution of the selective homogeneous ion-sensitive electrodes, e.g. a silver/silver iodide reference electrode in the case of an iodide-selective electrode, are not stable in the function of time, and consequently the apparent normal potential of the electrode changes in the course of measurements.

The construction of the selective halide- and sulfide-elective electrode according to the present invention is such as to compensate for the effect of thermal dilatation and consequently no cracks develop at the contact surface of the sensor block and the plastic electrode body so that no "memory effect" will occur and the response time is reduced to 10–20 seconds.

The thermal expansion-compensating property of the electrode also results in the fact that the electrodes can be applied at temperatures higher by 20°–30° C than the electrodes known up to now.

Construction of the sensor of the electrode in the form of a block of spherical curvature rather than in the form of a membrane, and finishing of the sensor block by isothermal recrystallization result in a striking new technical effect inasmuch as the solubility product of the precipitate which is the material of the specially polished, spherical-surface sensor block is lower than that of the known precipitate wafer having edges and apices. In view of the above, the sensitivity of the electrode is increased; the lower limit of the measuring range of the electrode is decreased by about one order of magnitude as compared to the known halide- and sulfide-sensitive electrodes, that is to say, the measuring range of the electrode is increased by one order of magnitude. (As to the connection between solubility product and lower limit of measuring range, reference is made to the literature; cf Havas, J.: Ion-Selective Micro-Capillary Solid Membrane Electrodes. *Chemical Communications of the Hungarian Academy of Sciences*, Vol. 37, pp. 315–350. 1972)

In order to support the above statements, FIG. 1 shows measured results: electromotive force values plotted against bromide ion activity. Curve 1 shows results obtained with an electrode equipped with a sensor of the shape of a circular plate; curve 2, those obtained with one equipped with a sensor made of silver bromide of spherical surface; and Curve 3, those obtained with an electrode equipped with a sensor of spherical surface composed of silver bromide-silver-silver chloride precipitate layers. It is apparent that the order of the lower limit of the measuring range corresponds to curves $1 > 2 > 3$.

A further advantageous property of the selective halide- and sulfide-sensitive electrodes according to the present invention is that they allow the construction of a potentiometric measuring cell without the liquid junction, thereby making possible measurements without having to carry out diffusion potentials. This effect is reached in such a manner that the sensor is constructed in a laminar structure along the longitudinal axis. For example, the case of a bromide-selective electrode, the construction is such that the silver bromide layer on the side of the sample solution contacts a metallic silver layer, impermeable for the ions, and the silver layer, in turn, contacts a layer of silver chloride precipitate. The laminar construction of the sensor block involves a further advantage, inasmuch as the quality and concentration of the electrolyte solution of constant ion concentration in contact with the sensor block can be chosen identical in the case of all of the electrode types; similarly, it is possible to apply a reference electrode of the same kind, e.g. a silver-silver chloride reference electrode, of a potential known and constant in time, in the solution in the case of all types of electrodes. This arrangement allows the selective halide- and sulfide-sensitive electrodes to be realized on the basis of the same construction principle and to produce electrodes whose apparent normal potential does not change in time.

Figure 2:
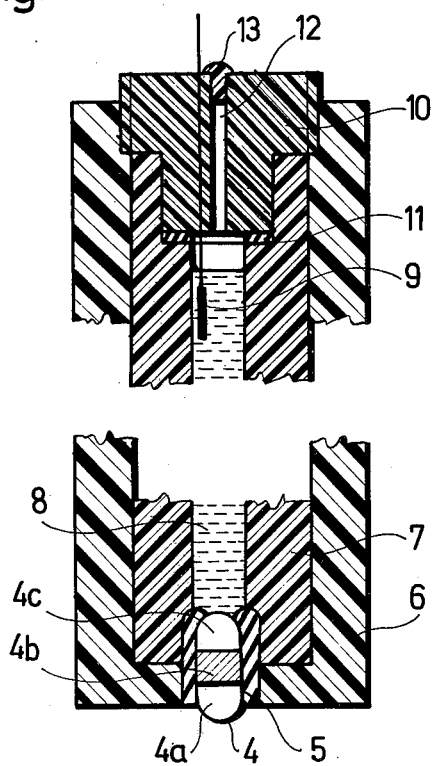

A more detailed description of the preferred embodiment of the present invention follows:

The laminar structure of the spherical sensor is built up of layers 4A, 4B, and 4C as illustrated in the drawing, FIG. 2. These layers are perpendicular to the longitudinal axis thereof and the material of these layers consists of a metal halide or a mixture of metal halides, a metal sulfide or a mixture of metal sulfides or a mixture of metal halides and metal sulfides, with the proviso that the metal layer is between the two metal salt layers or on the side which faces the potential carrier away, i.e toward the interior of the electrode. This metallic component can be, for example, silver, copper, cadmium, lead or a lanthanide. Thus, the precipitate which forms the material of the block is, for example, a silver halide, lanthanum halide, silver sulfide, copper sulfide, cadmium sulfide, lead sulfide or lanthanum fluoride.

The block or the layers thereof, 4A, 4B, and 4C comprised of the above materials are each preferably built up of a single crystal. Thus, the monocrystalline layers are consolidated into a block with the metal layer. This is done mechanically, for example, by the aid of the structure shown in FIG. 2. The silicone rubber 5 and the electrode bodies 6 and 7 are mechanically attached to each other.

The surface of said block is mechanically polished followed by isothermal recrystallization. Mechanical polishing takes place before the isothermal recrystallization. The mechanical polishing is carried out in the usual manner by employing polishing materials of varying particle size.

In the manufacture of the sensor of ion selective electrodes the last mechanical step is the formation of the shape of the sensor. As in the case of all mechanical processes, superficial edges and inequalities, apices, are formed depending on the shape and surface of the polishing tool. It is well known from the basic laws of physics that the ions located at the edges and peaks, for energetical reasons, tear loose more easily from the solid phase than those which are disposed at surface areas which have no peaks or edges. Therefore, there is a differential in the rate of solubility and in the value of the solubility product. This is proven, for example, by the diagram shown in the description of the invention FIG. 1. The semi-spherically shaped surface and the isothermal recrystallization step assures the ultimate elimination of the edges and peaks on the sensor surface.

The components of the layers 4A, 4B and 4C are the followings:

layer 4A: silver chloride, silver bromide, silver ionide, silver sulfide, copper sulfide, cadmium sulfide, lead sulfide, lanthanum fluoride,
  a mixture of silver chloride /10-90%/, and silver sulfide /90-10%/;
  a mixture of silver bromide /10-90%/ and silver sulfide /90-10%/;
  a mixture of silver iodine /10-90%/ and silver sulfide /90-10%/;
  a mixture of silver chloride /10-90%/ and silver bromide /90-10%/;
  a mixture of silver chloride /10-90%/ and silver iodine /90-10%/;
  a mixture of silver bromide /10-90%/ and silver iodine /90-10%/;
  a mixture of copper sulfide /10-90%/ and silver sulfide /90-10%/;
  a mixture of cadmium sulfide /10-90%/ and silver sulfide /90-10%/;
  a mixture of lead sulfide /10-90%/ and silver sulfide /90-10%/ while the concentration ratio in the mixture is preferably 70:30.

layer 4B: silver, copper, cadmium, lead, lanthanide and all components of layer 4A.

layer 4C: silver, copper, cadmium, lead, lanthanide and all components of layer 4A.

The indicated percentagues are mass percents.

Isothermal recrystallization of the sensor of the electrode is carried out by contacting the sensor of the electrode with a continuous stream of a saturated solution of the electrode sensor material at constant temperature for a predetermined time. This operation is continued as long as the edges and surface irregularities vanish entirely. In view of the construction of the electrode in the case of a semi-spherically shaped sensor, there is no possibility for the re-formation of peaks and irregularities, while in the case of electrodes having a planar membrane, new ridges are formed in the vicinity of the point of attachment because of the later dissolution of the material of the electrode during its use.

The design of the selective halide- and sulfide-sensitive electrodes is, as an example, presented in the following together with the process for the preparation of same. It is understood, however, that the protection of the invention is not restricted to the examples.

EXAMPLE 1

FIG. 2 shows the structure of the selective bromide- and sulfide-sensitive electrodes in longitudinal section. Sensing Block 4 of spherical surface, built up of silver bromide or silver sulfide layer 4A, metallic silver layer 4B and silver chloride layer 4C, is in contact with elastic insulating layer 5 — preferably of silicone rubber — which fits into the wall portion, parallel to the surface of sensor Block 4, of outer 6 and 7 electrode bodies made of a plastic material, preferably PVC.

The cavity of internal electrode body 7 contains electrolyte solution 8 containing $10^{-1}$ M potassium chloride. A silver/silver chloride reference electrode 9 is immersed into electrolyte solution 8. Internal electrode body 7 is secured to external electrode body 6 by plastic — preferably PVC — plug 10. There is a silicone rubber O-ring 11 between internal electrody body 7 and plug 10. There is an opening 12 in plug 10, covered by closure cap 13.

EXAMPLE 2

First of all, sensor block 4 is prepared according to the following: a dry silver chloride precipitate powder, containing neither silver nor bromide ions in excess, a dry colloidal silver powder and a silver chloride powder containing neither silver nor chloride ions in excess are laminated upon each other and pressed at a pressure of 14,000 – 16,000 at to a cylinder of 6 mm in diameter. A piece, 13 mm in length is cut of silicone rubber tubing, 5/4 mm in diameter and placed into analytical grade petrol for a period of 10 minutes. The swollen piece of tubing is symmetrically pulled up on sensor block 4. Sensor block 4 equipped with silicone rubber insulating layer 5 is kept at a temperature of 50° C for a period of 2 hours. After the removal of petrol, internal 6 and external 7 electrode bodies shaped in accordance with FIG. 2 are kept at a temperature of 40°-50° C for a period of 1 hour. After 1 hour, sensor block 4 equipped with insulating layer 5 is placed into the warm external electrode body 6 in such a manner that the longitudinal axis of sensor block 4 is parallel to the longitudinal axis of external electrode body 6 and the silver bromide layer is adjacent to the sample solution. Internal electrode body 7 is fitted into external electrode body 6. Silicone rubber O-ring 11 is put into place and electrode bodies 6 and 7 are secured by plug 10 incorporating silver-silver chloride electrode 9. Solution 8, of a cncentration 1 M with respect to potassium chloride, is injected into the internal cavity of electrode body 7 through opening 12. The latter is sealed by closure cap 13. The electrode prepared according to the foregoing is allowed to stand for a period of 1 day. The piece of silicone rubber protruding from external electrody body 6 is cut off. Hereupon, the end of the electrode containing sensor block 4 is placed into streaming distilled water of 37.0° C temperature being saturated by the said electrode sensor material for a period of 48-50 hours. Upon completion of the above-mentioned operation, a sensitive selective bromide-sensitive electrode possessing a surface polished by isothermal recrystallization is obtained.

What we claim is:

1. Selective halide- and sulfide- sensitive electrode for the determination of halide and sulfide ion concentrations and activities in solution having a solid sensor built up of a halide and/or sulfide precipitate, and an electrode body built in such a manner that one surface portion of the sensor contacts the sample solution whereas another surface portion of the sensor, isolated by the electrode body from the portion in contact with the sample, contacts an electrolyte solution of constant ion concentration, the latter being equipped with a potential outlet terminal, comprising a sensor in the form of a solid block, the surface portion of said block contacting the sample solution being spherical or of a curved surface void of edges or apices; the surface portion of said block not contacting the sample solution or the solution of constant ion concentration being connected to an elastic layer, which in turn is in contact with the wall of a tubular plastic electrode body, wherein said block is built up of three layers perpendicular to the longtitudinal axis thereof, the materials of the layers being a metal halide or a mixture of metal halides, a metal sulfide or a mixture of metal sulfides or a mixture of metal halides and metal sulfides, with the proviso that a metal layer is between the two metal salt layers.

2. A halide- and sulfide-sensitive electrode as claimed in claim 1, wherein the metallic component of the material of said block is silver, copper, cadmium, lead or a lanthanide.

3. A selective halide- and sulfide-sensitive electrode as claimed in claim 1, wherein the precipitate which forms the material of the block is silver halide, lanthanum halide, silver sulfide, copper sulfide, cadmium sulfide, lead sulfide or lanthanum sulfide.

4. A selective halide- and sulfide-sensitive electrode as claimed in claim 1 wherein the surface of the block is mechanically polished and isothermally recrystallized.

* * * * *